US006652143B2

United States Patent
Popescu

(10) Patent No.: US 6,652,143 B2
(45) Date of Patent: Nov. 25, 2003

(54) METHOD AND APPARATUS FOR MEASURING THE POSITION, SHAPE, SIZE AND INTENSITY DISTRIBUTION OF THE EFFECTIVE FOCAL SPOT OF AN X-RAY TUBE

(75) Inventor: Stefan Popescu, Erlangen (DE)

(73) Assignee: Siemens Aktiengesellschaft, Münich (DE)

( * ) Notice: Subject to any disclaimer, the term of this patent is extended or adjusted under 35 U.S.C. 154(b) by 299 days.

(21) Appl. No.: 09/834,289

(22) Filed: Apr. 12, 2001

(65) Prior Publication Data
US 2002/0159566 A1 Oct. 31, 2002

(51) Int. Cl.[7] .......................... G01D 18/00; A61B 6/08
(52) U.S. Cl. ............................................. 378/207
(58) Field of Search ...................... 378/113, 204, 378/205, 206, 207, 101; 250/252.1; 356/123

(56) References Cited

U.S. PATENT DOCUMENTS

| | | | | |
|---|---|---|---|---|
| 5,745,548 A | * | 4/1998 | Dobbs et al. ................ | 378/207 |
| 6,091,797 A | * | 7/2000 | Xie et al. .................... | 378/62 |
| 6,310,938 B1 | * | 10/2001 | Toth et al. .................. | 378/147 |
| 6,327,329 B1 | * | 12/2001 | Bromberg et al. ........... | 378/19 |
| 6,343,110 B1 | * | 1/2002 | Li ................................ | 378/19 |
| 6,449,340 B1 | * | 9/2002 | Tybinkowski et al. ....... | 378/150 |
| 2002/0021785 A1 | * | 2/2002 | Toth et al. .................. | 378/147 |
| 2002/0181661 A1 | * | 12/2002 | Vafi et al. .................... | 378/207 |
| 2003/0007601 A1 | * | 1/2003 | Jaffray et al. ................ | 378/65 |

OTHER PUBLICATIONS

E. Krestel, "Imaging Systems for Medical Diagnostics", pp. 222–232. 1990.

* cited by examiner

*Primary Examiner*—Eric S. McCall
(74) *Attorney, Agent, or Firm*—Schiff Hardin & Waite (57) ABSTRACT

In a method and apparatus for dynamically measuring the position, shape, size and intensity distribution of an effective focal spot of an x-ray tube, wherein at least one of these characteristics changes with respect to time, a detector array is provided that is composed of a number of detector elements, and a micro-hole collimator is disposed between the focal spot and the detector array at a distance closer to the focal spot than to the detector array. An x-ray beam emitted from the focal spot passes through an aperture in the micro-hole collimator, and produces a magnified projection of the focal spot on the detector array. The respective electrical signals from the detector elements of the detector array are sampled, and these sampled signals are combined to dynamically measure the position, shape, size and intensity distribution of the focal spot.

14 Claims, 6 Drawing Sheets

METHOD AND APPARATUS FOR MEASURING THE POSITION, SHAPE, SIZE AND INTENSITY DISTRIBUTION OF THE EFFECTIVE FOCAL SPOT OF AN X-RAY TUBE

BACKGROUND OF THE INVENTION

1. Field of the Invention

The present invention is directed to a method and apparatus suitable for measuring the position, shape, size and intensity distribution of the effective focal spot of an x-ray tube, particularly a computed tomography (CT) x-ray tube.

2. Description of the Prior Art

The stability of the position, size and intensity of the focal spot of an x-ray tube in a CT apparatus depends on many factors, including the mechanical tolerances of the anode surface and its dynamic stability, as well as the precision with which the electron beam, and its intensity distributions on the anode surface, can be controlled. The combined effects of tolerance deviations and electron beam divergence produce an electronic focal spot (hot spot) on the anode surface that varies over time with regard to one or more of the aforementioned characteristics. The position and intensity distribution of the hot spot yield the modulation transfer function (MTF), which is a fundamental measure of the imaging properties of the focal spot. Usually, the effective size of the focal spot is defined as the projection of the hot spot in the imaging direction perpendicular to the tube axis.

A newer type of computed tomography x-ray tube provides for active toggling of the focal spot position (flying focal spot system) to increase the sampling density. These tubes use magnetic deflection of the electron beam to toggle the focal spot position. Another newer type of CT x-ray tube, which is a rotating bulb tube wherein the bulb is piston-shaped, uses active magnetic deflection of the electron beam to bend the electron beam and keep it on the hot track. In x-ray tubes of this type, the effective size and shape of the focal spot depend additionally on the homogeneity and stability of the magnetic field used to deflect the electron beam.

In view of the multitude of factors which influence the aforementioned characteristics of the focal spot, there is a need for a simple apparatus to measure the size and shape of the effective focal spot, as well as its intensity distribution. It would be desirable to be able to make static or dynamic corrections, as needed, based on the information obtained with respect to the shape, size and intensity distribution.

A conventional approach employed for measuring the size of the focal spot is based on the generation of a pinhole camera-type image, as described in "Imaging Systems For Medical Diagnostics," Krestel, Ed., Siemens A G (1990), pages 230–231. This known technique is inappropriate, however, for measurements of the intensity distribution, because it is unable to correct for the inherent aperture errors which arise due to the finite diameter of the hole in the collimator through which the x-ray beam passes. Moreover, additional errors arise due to parasitic radiation, which may pass through the collimator material because the collimator may not be thick enough to completely attenuate such parasitic radiation. Consequently, this known technique has disadvantages associated therewith with regard to obtaining a good compromise between the hole diameter, the collimator thickness, and the total errors.

For a more exact analysis of the focal spot, at least with respect to its intensity distribution, other known techniques employ passing the x-ray beam through narrow slits oriented along the two major axes of the focal spot. The images obtained in this manner are analyzed with a photometer so as to measure the intensity distribution of the x-rays in the focal spot. This is also described in the aforementioned Imaging Systems For Medical Diagnostics text. This technique, however, is not appropriate for use to dynamically measure the shape and position of a focal spot which change over time such as, for example, because of rotation of the anode. Moreover, measurements obtained in this known manner cannot be used in the context of an automatic adjustment procedure for actively modifying the size and shape of the focal spot such as during a calibration phase.

SUMMARY OF THE INVENTION

It is an object of the present invention to provide a method and an apparatus for measuring the position, shape, size and intensity distribution of the effective focal spot of an x-ray tube which avoids, or at least minimizes, the aforementioned errors associated with known techniques and devices, and which is suited for use for automatically modifying one or more of the aforementioned parameters in an adjustment procedure.

The above object is achieved in accordance with the principles of the present invention in a method and apparatus for dynamically measuring the position, shape, size and intensity distribution of an effective focal spot of an x-ray tube, wherein at least one of the aforementioned characteristics changes with respect to time, wherein a detector array is provided that is composed of a number of detector elements, each of which generates an electrical signal dependent on x-rays incident thereon, and wherein a micro-hole collimator is disposed between the focal spot and the detector array at a location closer to the focal spot than to the detector array. When an x-ray beam is emitted from the focal spot, it passes through the aperture in the micro-hole collimator and a projection of the focal spot is produced on the array. Since the collimator is located closer to the focal spot than to the detector array, a magnification factor or zoom factor is achieved, which is defined by the ratio of the distance between the collimator and the detector array, and the distance between the focal spot and the collimator. Since the collimator is located closer to the focal spot than to the detector array, this magnification factor is greater than 1. Each of the detector elements of the detector array emits an electrical signal corresponding to the radiation incident thereon.

Since the respective output signals of the elements of the detector array are dependent on the intensity of the radiation incident on the detector element, the intensity distribution of the projected image, and thus of the focal spot, can be determined along any selected direction. The number of completely irradiated elements of the detector array, plus the respective detector elements which are partially irradiated which are located at the periphery of the projection, indicate the size and shape of the projected image, and thus of the focal spot. Since the output signals from the respective detector elements can be monitored over time, changes in these output signals, which in turn indicate changes in one or more of the aforementioned characteristics of the focal spot, can be easily monitored and identified.

DESCRIPTION OF THE PREFERRED EMBODIMENTS

Figure 1:
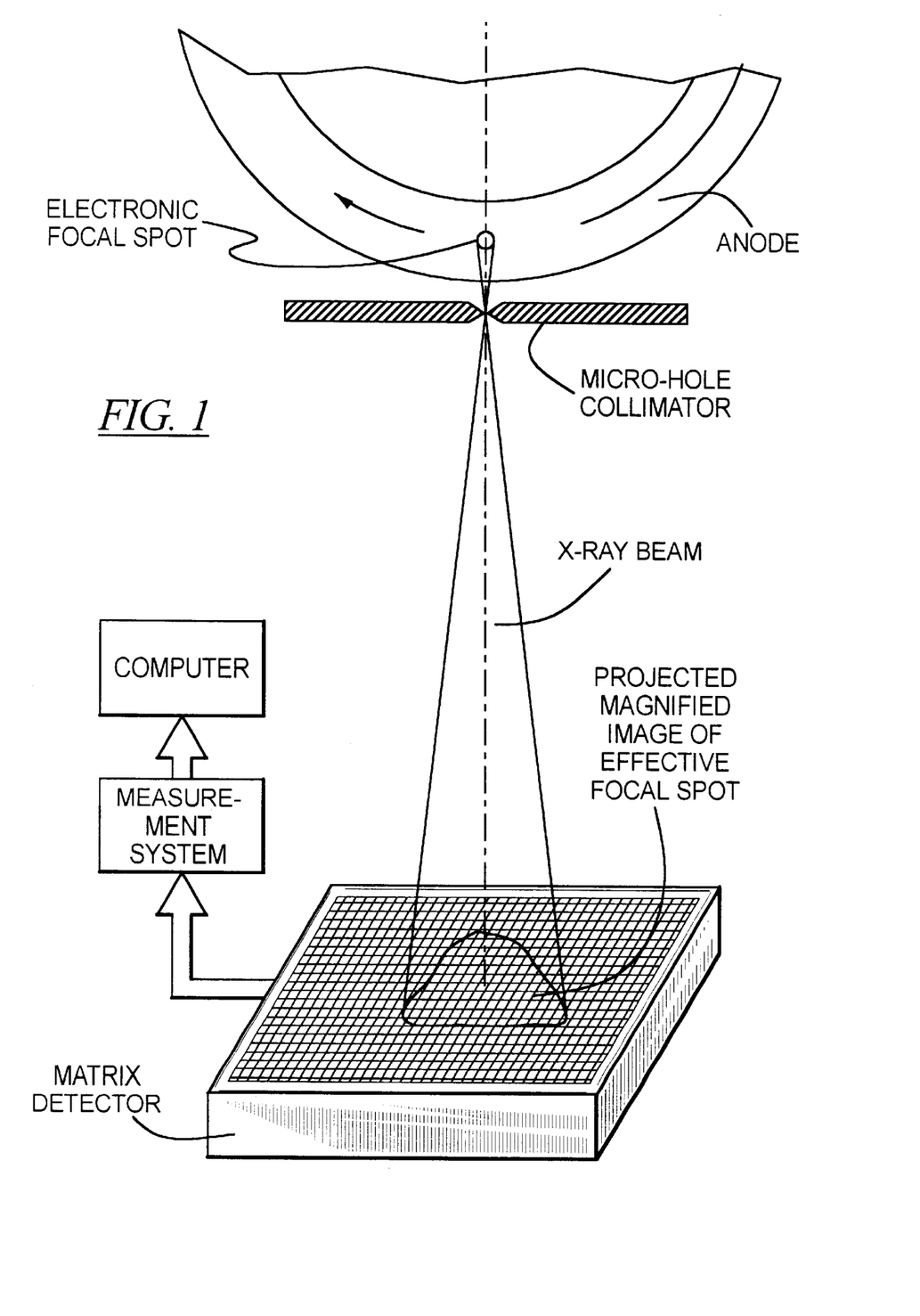
FIG. 1 is an illustration showing the basic components of an apparatus for dynamically measuring a position, shape, size and intensity distribution of an effective focal spot of an x-ray tube in accordance with the invention, operating according to the inventive method.

In the inventive apparatus shown in FIG. 1, a plan view of a portion of an anode of an x-ray tube, in this case a rotating anode dish or plate, is shown on which an electron beam (not shown) is incident at an electronic focal spot. As a result of the interaction of the electrons in the electron beam with the anode, an x-ray beam is emitted, which is caused to pass through an aperture in a micro-hole collimator.

Figure 2:
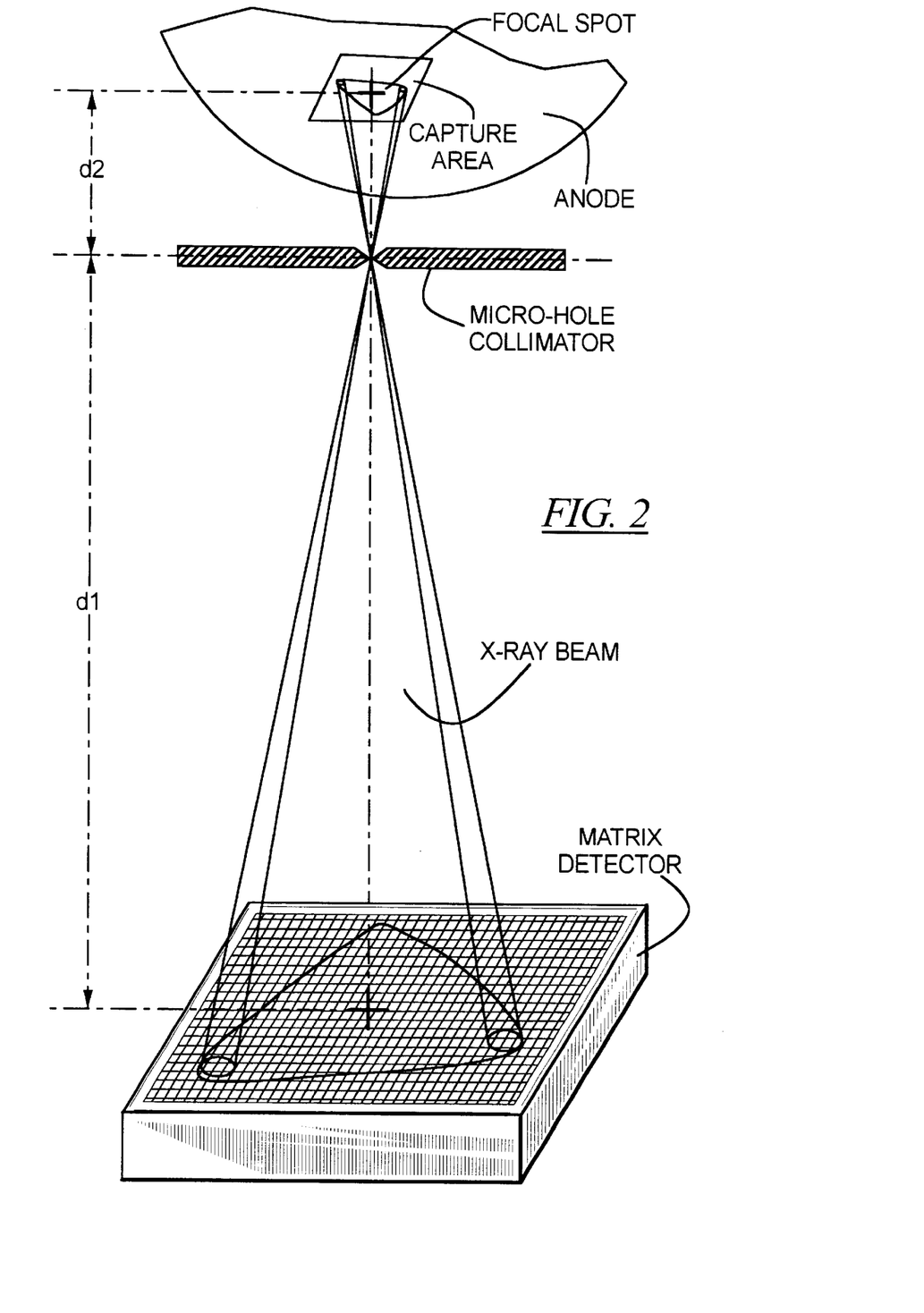
FIG. 2 illustrates the magnification or zoom factor which is achieved in accordance with the invention.

As explained in more detail in conjunction with FIG. 2, the x-ray beam is magnified and thereby produces a projected magnified image of the effective focal spot on a matrix detector. The matrix detector is composed of a large number of individual detector elements, each of which emits an electrical signal dependent on the radiation incident on the detector element. The electrical signals from all of the detector elements are supplied to a measurement system, which is able to identify the detector element, such as by row and column, which produce the output signal the measurement system identifies the amplitude of each output signal and converts this information into digital form. Digital signals representing all of the output signals from the matrix detector are supplied from the measurement system to a computer which analyzes the digital signals to obtain information identifying the position, size, shape and intensity distribution of the focal spot, from the projected magnified image thereof on the matrix detector.

Depending on the magnification factor and the available number of detector elements in the detector array, the projection on the surface of the detector array may exactly delimit the focal spot (although enlarged), or it may include a larger long-term focal spot "walking" or "wandering" area, as shown in FIG. 2.

The magnification factor is determined as follows. It is assumed for a first approximation that the collimator material provides infinitely high attenuation for the x-rays emitted from the focal spot, and that the collimator aperture is very small compared to the actual size of the focal spot. Under these circumstances, as shown in FIG. 2, each detector element of the detector matrix receives only radiation emerging from a small surface-element of the focal spot (the focal spot being theoretically divided into such elementary radiators). More particularly, each detector element in the matrix measures that radiation generated by a surface-element of the focal spot that corresponds to the compressed image of the detector surface projected optically through the collimator aperture over the anode surface.

As shown in FIG. 2, the zoom or magnification factor is the ratio of the distance $d_1$ between the collimator and the surface of the matrix detector, and the distance $d_2$ between the collimator and the focal spot. Expressed mathematically, the magnification factor thus is $d_1/d_2$.

Figure 5:
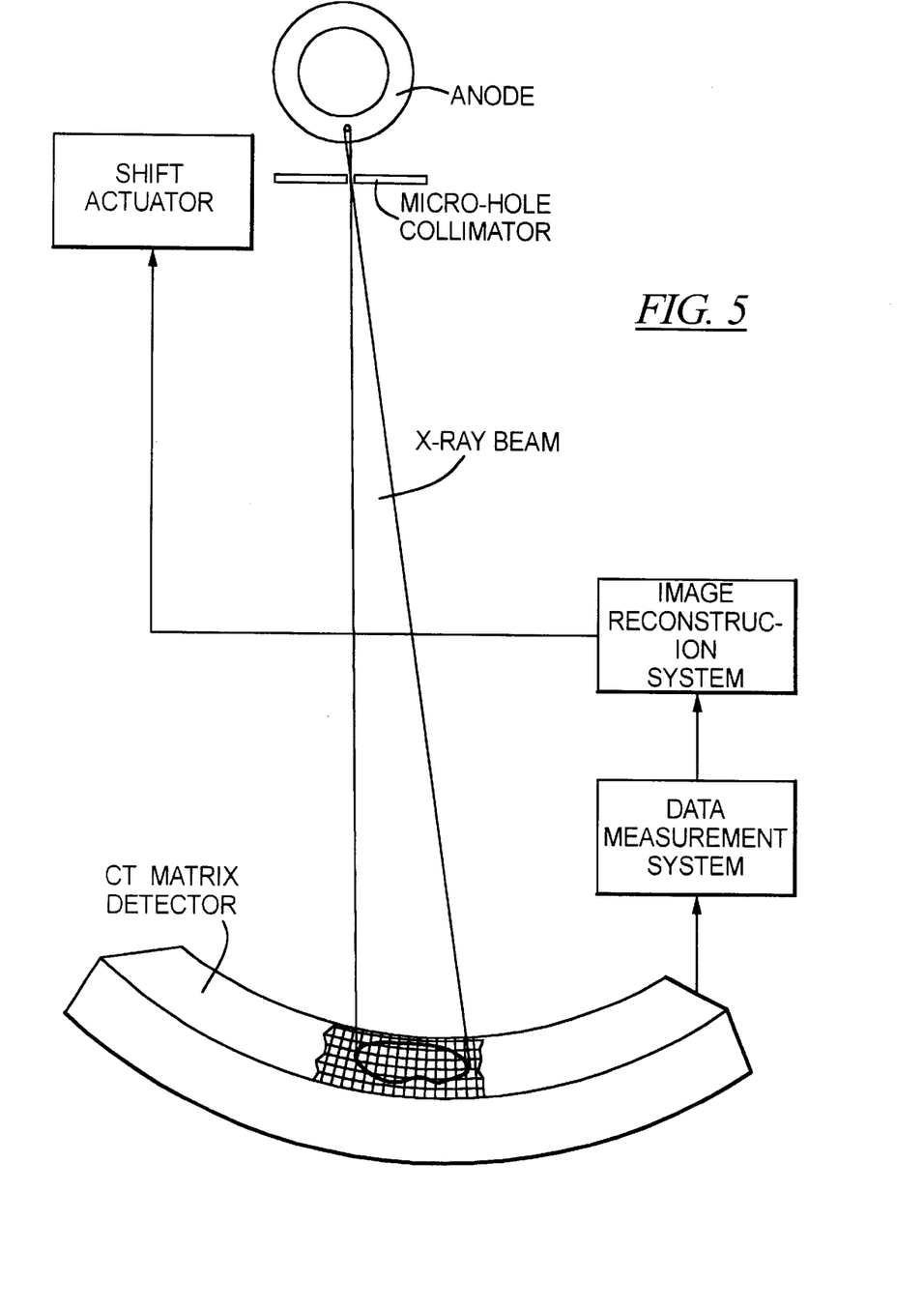
FIG. 5 illustrates the employment of the inventive method and apparatus in a computed tomography system.

The magnified image of the effective focal spot projected over the surface of the detector matrix can be sampled dynamically in the surface domain (shape and size) in the x-ray intensity domain, and in the time domain by the data measurement system and the computer. Particularly when the detector matrix is a standard CT detector matrix, the already-present CT measurement and computing system can be employed for undertaking the necessary measurements and calculations in a calibration phase, as shown in FIG. 5.

There are two basic sources of error associated with the magnifying micro-hole collimator shown in FIGS. 1 and 2.

Figure 3:
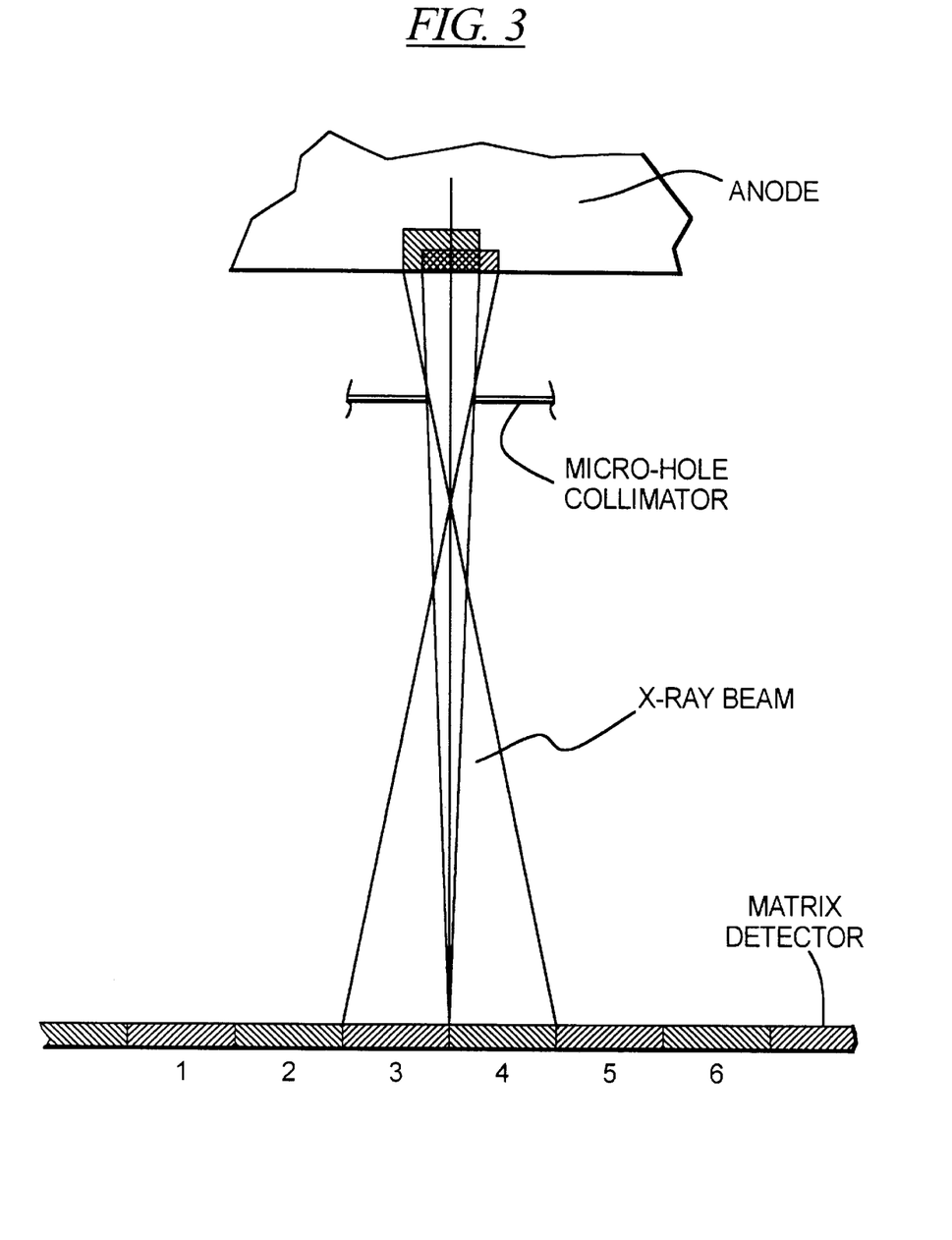
FIG. 3 illustrates the overlapping effect due to the finite size of the aperture in the collimator.

The first of these sources of errors is due to the fact that an ideal pinhole collimator should have an infinitely small aperture, which of course cannot be achieved as a practical matter. Since the "real life" collimator will have an aperture with a finite size, although small, this means that the projections of adjacent anode elementary radiators will overlap each other on the surface of the detector matrix, as shown in FIG. 3, thereby producing aperture errors and a blurred focus spot image. In order to have a good precision and accuracy, however, the diameter of the micro-collimator aperture must be negligibly small compared to the target sampling resolution. An aperture with a small diameter, however, reduces the number of radiation quanta which reach the detector surface, thereby increasing the noise and error in the measurements.

A second basic source of error arises because if the collimator aperture is made with a small diameter, this means that a very thin collimator must be used in order to enlarge the capture area sufficiently to cover the focus as well as the walking area of the focus. Because the collimator material has a limited attenuation for x-rays, the use of a thin collimator means that a significant number of radiation quanta will penetrate through the collimator and reach the matrix detector, together with the quanta passing through the aperture, thereby distorting the focal spot image on the detector.

The inventive method and apparatus are able to correct for both of these basic sources of error.

As noted above, the first of the two basic error sources arises because a real micro-hole collimator exhibits an aperture error because the projections of the detector elements of the detector matrix through the collimator aperture partially overlap on the anode surface. This means that two adjacent detector elements in the matrix may simultaneously receive quanta emitted from the same elementary (theoretical) division of the focus spot, as schematically illustrated in FIG. 3. The degree of overlapping depends on the geometrical arrangement of the micro-hole collimator and the detector matrix. Making the collimator aperture smaller can reduce the overlapping effect, but this also reduces the amplitude of the signals measured by the detector elements, and therefore increases the noise, thus inducing other measurement errors.

Figure 4:
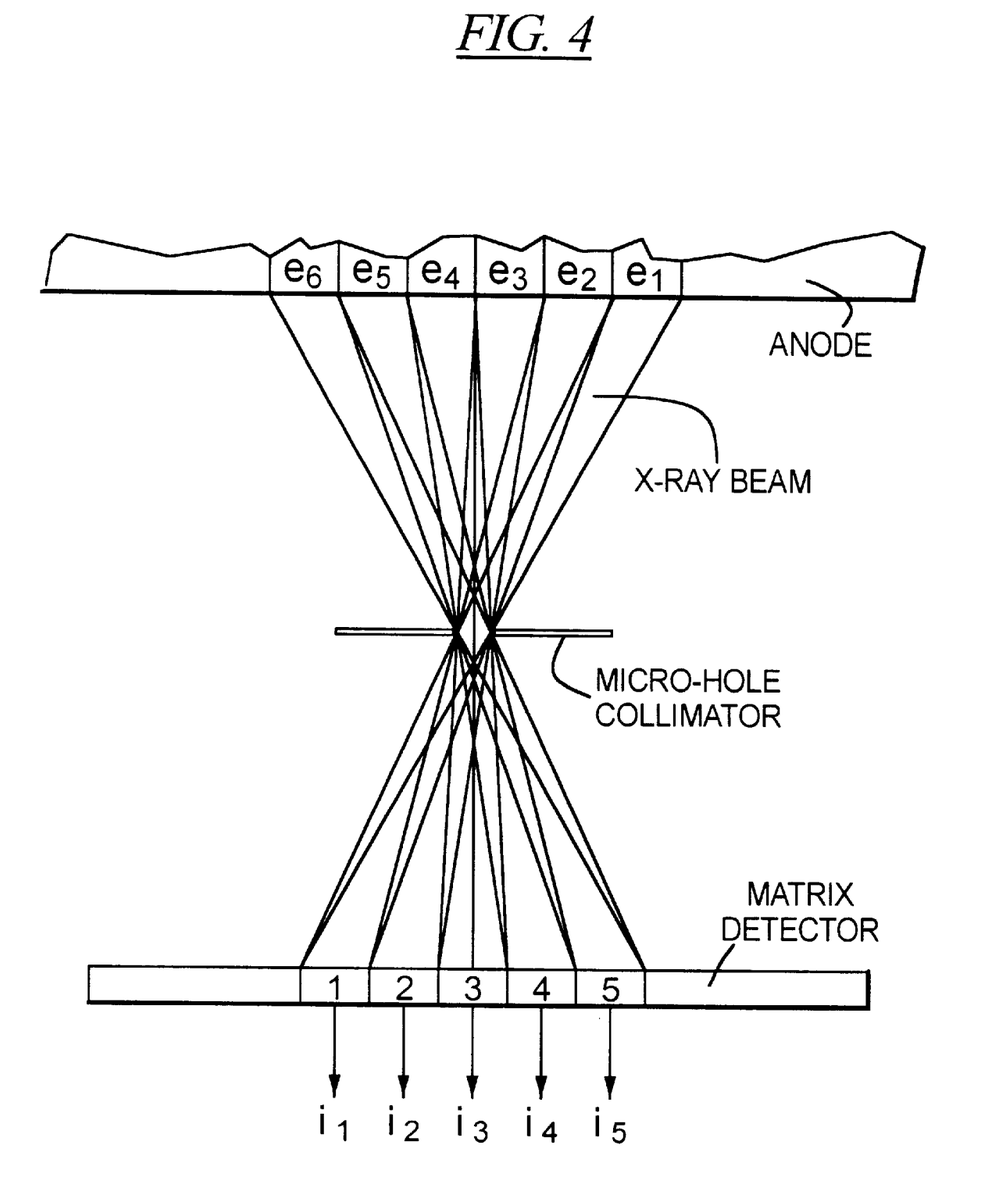
FIG. 4 illustrates the manner by which errors arising due to the overlapping illustrated in FIG. 3 are corrected in accordance with the inventive method and apparatus.

The inventive method and apparatus correct for these overlapping errors, while keeping the collimator aperture large enough to avoid significant noise in the detector element output signals. This is accomplished by producing a controlled overlapping factor, as shown in FIG. 4 of, for example, 50%. In this case, the micro-hole collimator must have an aperture diameter D according to the relation $$D = \frac{\text{detector resolution}}{\text{magnitication factor} + 1}$$

As an example, for a detector matrix with 1 mm×1 mm resolution, and a magnification factor of 10, the micro-hole collimator aperture must be 0.091 mm to obtain 50% overlapping.

In order to measure the surface intensity distribution of the focal spot, this overlapping error must be corrected. The inventive method and apparatus do so in two different ways.

Figure 6:
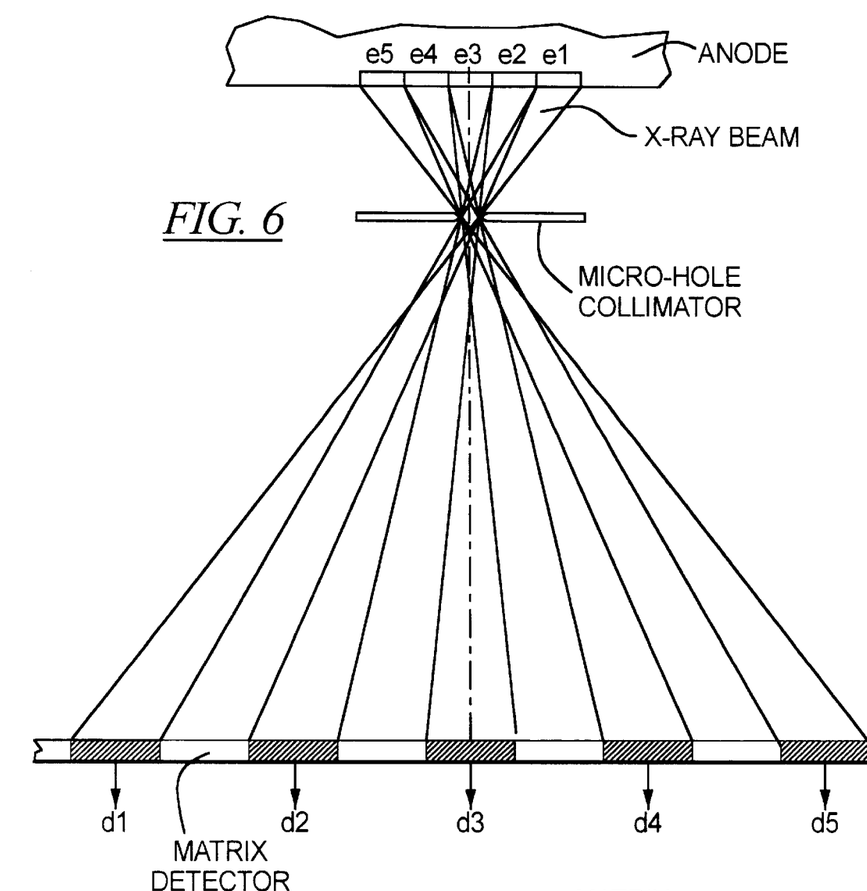
FIG. 6 is a side view of an embodiment of the inventive apparatus using a so-called "sparse" detector matrix to overcome the aforementioned
Figure 7:
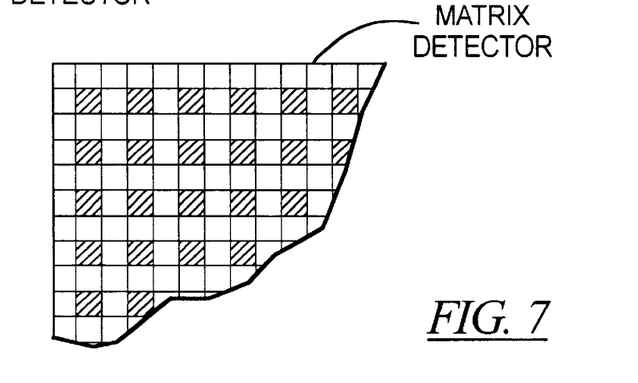
FIG. 7 is a plan view of a portion of the "sparse" detector matrix of FIG. 6.

As shown in FIGS. 6 and 7, when using a predetermined overlapping factor of, for example, 50%, it is possible to use a so-called "sparse" matrix detector, with non-signal generating gaps between the detector elements, so that each elementary radiator on the anode surface irradiates only a single detector element. For maximum accuracy, the coverage factor of the sparse detector matrix must be equal to the overlapping factor, as shown in FIG. 6 for 50% overlapping. When using a CT matrix detector (as shown in FIG. 5) as the image receptor for the 50% overlapping, a simple correction is possible by using the output signal from every other detector element in order to determine the image intensity of the focal spot. This means that the sampling resolution is reduced by half. For example, for a resolution of 20×20 detector elements, the resolution achieved in sampling the focal spot intensity is 10×10. Moreover, the magnification factor is reduced by half as well, i.e., for a geometrical magnification factor of 4, the resulting magnification factor will be 2.

Another way that the inventive method overcomes the overlapping effect, but preserves the available sampling resolution and precision, is to use a simple arithmetic correction. For explaining this correction procedure, a one-dimensional vector detector is assumed, with five channels and a magnification factor of unity. For 50% overlapping, the micro-hole collimator aperture is one-half of the size of the detector window, as illustrated in FIG. 4. The projection of each detector element on the anode emitting surface is twice as large as the detector window, and the investigated area on the anode is (theoretically) divided into six linear elements, respectively emitting radiation at intensities $e_1$ through $e_6$. The respective output signals of the detector elements are indicated as $i_1$ through $i_5$. Each detector element receives radiation quanta from two adjacent emitters, which can be expressed as $i_k = e_k + e_{k+1}$, wherein k=1 ... 5.

Considering the focal spot intensity to be negligible at the margin of the investigated area ($e_6 = 0$, thus if there are m linear elements, k=m−1), the intensity distribution of the focal spot is then obtained by solving the linear system of equations $e_k = i_k - e_{k-1}$, wherein k=5 ... 1.

The same solution can be extrapolated for a two-dimensional analysis of the focal spot intensity distribution.

The inventive method and apparatus compensates for errors produced by "out of aperture" radiation which penetrates through the collimator, as follows. As noted above, the matrix detector receives radiation passing through the collimator aperture as well as a certain amount of additional radiation that penetrates through the collimator material itself. This out of aperture radiation reaches the matrix detector at locations where only "in aperture" radiation is expected. This parasitic radiation thus distorts the projected focal spot image.

In order to eliminate this error, the inventive method undertakes a correction based on image subtraction. As shown in FIG. 5, a shifting actuator is employed to shift the position of the collimator. The collimator is first shifted laterally so that the micro-hole is positioned outside the capture area of the matrix detector. Radiation is emitted from the focal spot, and in this case the detector matrix is irradiated only by out of aperture radiation which penetrates through the material of the collimator. The output signals from the detector elements under this condition are obtained by the measurement system and are stored in the computer. The collimator is then shifted so that the x-ray beam nominally passes through the aperture in the micro-hole collimator, and output signals from the detector elements are again recorded. By subtracting the two stored energy images, an image is produced which represents only the effect of the collimator aperture, without the out of aperture radiation, and thus this image is an undistorted focal spot image. The collimator has a uniform thickness throughout, in order to avoid additional errors from arising as a result of the aforementioned shifting.

As noted above, the method and apparatus are suitable for dynamically measuring the size and position of a wandering or walking focal spot, wherein these characteristics change over time. For this purpose, the aforementioned overlapping error are ignored, and the magnification factor is reduced so as to allow the matrix detector to capture the entire expected area of wander of the focal spot. This measurement arrangement is shown in FIG. 5 for a CT apparatus, except that the projection of the focal spot covers a smaller area of the matrix, for example, 2×2 detector elements. The computer identifies the wandering area of the focal spot by analysing the individual detector output signals.

It will be understood by those of ordinary skill in the art that departures from the above-described exemplary embodiments can be undertaken without departing from the scope of the invention. For example, for a magnification factor of 15, the micro-hole collimator will be positioned 150 mm from the focal spot, and 1500 mm from the detector matrix.

In CT systems using a matrix detector with a resolution of 1×1 mm in the center, with 20×20 elements, provides a total sampling area of 2×2 mm around the focal spot, with a sampling resolution of 0.1×0.1 mm. In this case, the aperture of the micro-hole collimator must be 0.625 mm for 50% overlapping.

Although modifications and changes may be suggested by those skilled in the art, it is the intention of the inventor to embody within the patent warranted hereon all changes and modifications as reasonably and properly come within the scope of his contribution to the art.

I claim as my invention:

1. A method for dynamically measuring a position, shape, size and intensity distribution of an effective focal spot on an anode of an x-ray tube, wherein at least one of said position, shape, size and intensity distribution changes with respect to time, comprising the steps of:

theoretically dividing said focal spot into a plurality of elementary radiators;

providing a detector array having a resolution, said detector array being composed of a plurality of detector elements, each of said detector elements generating an electrical signal dependent on x-rays incident thereon;

disposing a micro-hole collimator between said focal spot and said detector array at a distance closer to said focal spot than to said detector array;

emitting an x-ray beam from said focal spot which passes through an aperture in said micro-hole collimator to produce a magnified projection of said focal spot on said detector array containing elementary protections produced by overlapping elementary radiators;

sampling respective electrical signals from said detector elements while said magnified projection is incident on said detector array, and combining said respective electrical signals to dynamically measure said position, shape, size and intensity distribution of said focal spot; and setting a diameter of said aperture in said micro-hole collimator through which said x-ray beam passes to substantially avoid significant noise in said electrical signals from said detector elements by setting said overlapping to a predetermined amount depending on said detector resolution and a magnification factor associated with said location of said micro-hole collimator.

2. A method as claimed in claim 1 comprising setting said overlapping to 50%.

3. A method as claimed in claim 1 wherein the step of combining said respective electrical signals comprises combining selected ones of said respective electrical signals dependent on the overlapping which is set.

4. A method as claimed in claim 3 comprising setting said overlapping at 50%, and combining respective electrical signals from detector elements separated from each other by one detector element.

5. A method as claimed in claim 1 comprising theoretically dividing said focal spot into a plurality of linear rows, each containing m elementary radiators, with each elementary radiator emitting radiation at an intensity $e_k$, wherein k=1 . . . m−1, and wherein each detector element of said detector array receives radiation from adjacent ones of said elementary radiators in each of said rows and emits said electrical signal as $I_k = e_k + e_{k+1}$, and determining said intensity distribution of said focal spot by solving a linear system of equations comprising $e_k = I_k - e_{k+1}$.

6. A method as claimed in claim 1 comprising employing a standard CT detector of a computed tomography apparatus for obtaining said magnified projection of said focal spot, and combining said respective electrical signals in a computer of said computed tomography apparatus.

7. A method for dynamically measuring a position, shape, size and intensity distribution of an effective focal spot on an anode of an x-ray tube, wherein at least one of said position, shape, size and intensity distribution changes with respect to time, comprising the steps of:

providing a detector array composed of a plurality of detector elements, each of said detector elements generating an electrical signal dependent on x-rays incident thereon;

disposing a micro-hole collimator between said focal spot and said detector array at a distance closer to said focal spot than to said detector array;

emitting an x-ray beam from said focal spot which passes through an aperture in said micro-hole collimator to produce a magnified projection of said focal spot on said detector array;

sampling respective electrical signals from said detector elements while said magnified projection is incident on said detector array, and combining said respective electrical signals to dynamically measure said position, shape, size and intensity distribution of said focal spot; and mechanically laterally shifting said micro-hole collimator so that a central ray of said x-ray beam is not directly aligned with said aperture and obtaining an image produced by said x-ray beam on said detector array, and laterally re-shifting said micro-hole collimator so that said central ray of said x-ray beam is directly aligned with said aperture and obtaining said magnified projection of said focal spot on said detector array, and subtracting said image from said magnified projection to compensate for radiation quanta proceeding through material of said micro-hole collimator.

8. A method as claimed in claim 7 comprising employing a standard CT detector of a computed tomography apparatus for obtaining said magnified projection of said focal spot, and combining said respective electrical signals in a computer of said computed tomography apparatus.

9. An apparatus for dynamically measuring a position, shape, size and intensity distribution of an effective focal spot on an anode of an x-ray tube, said focal spot being theoretically divisible into a plurality of elementary radiators, wherein at least one of said position, shape, size and intensity distribution changes with respect to time, comprising:

a detector array composed of a plurality of detector elements, each of said detector elements generating an electrical signal dependent on x-rays incident thereon, said detector array having a resolution;

a micro-hole collimator disposed between said focal spot and said detector array at a distance closer to said focal spot than to said detector array, said micro-hole collimator having an aperture therein;

means for emitting an x-ray beam from said focal spot which passes through said aperture in said micro-hole collimator to produce a magnified projection of said focal spot on said detector array containing elementary radiator projections produced by overlapping elementary radiators;

circuitry connected to said detector array for sampling respective electrical signals from said detector element while said magnified projection is incident on said detector array to obtain sampled signals;

said aperture in said micro-hole collimator throuah which said x-ray beam passes having a diameter to substantially avoid significant noise in said electrical signals from said detector elements, said diameter being dependent on a predetermined amount of said overlapping depending on said detector resolution and a magnification factor associated with said location of said micro-hole collimator; and a computer supplied with said sampled signals for combining said sampled signals to dynamically measure said position, shape, size and intensity distribution of said focal spot.

10. An apparatus as claimed in claim 9 wherein said overlapping is 50%.

11. An apparatus as claimed in claim 9 wherein said computer combines selected ones of said sampled signals dependent on said overlapping.

12. An apparatus as claimed in claim 11 wherein said overlapping is 50%, and wherein said computer combines sampled signals from respective detector elements separated from each other by one detector element.

13. An apparatus as claimed in claim 9 wherein said focal spot is theoretically divided into a plurality of linear rows, each containing m elementary radiators, with each elementary radiator emitting radiation at an intensity $e_k$, wherein k=1 . . . m−1, and wherein each detector element of said detector array receives radiation from adjacent ones of said elementary radiations in each of said rows and emits said electrical signal as $i_k=e_k+e_{k+1}$, and wherein said computer determines said intensity distribution of said focal spot by solving a linear system of equations comprising $e_k=i_k-e_{k+1}$.

14. An apparatus for dynamically measuring a position, shape, size and intensity distribution of an effective focal spot on an anode of an x-ray tube, wherein at least one of said position, shape, size and intensity distribution changes with respect to time, comprising:

a detector array composed of a plurality of detector elements, each of said detector elements generating an electrical signal dependent on x-rays incident thereon;

a micro-hole collimator disposed between said focal spot and said detector array at a distance closer to said focal spot than to said detector array, said micro-hole collimator having an aperture therein;

means for emitting an x-ray beam from said focal spot which passes through said aperture in said micro-hole collimator to produce a magnified projection of said focal spot on said detector array; and circuitry connected to said detector array for sampling respective electrical signals from said detector elements while said magnified projection is incident on said detector array to obtain sampled signals;

a computer supplied with said sampled signals for combining said sampled signals to dynamically measure said position, shape, size and intensity distribution of said focal spot; and an actuator for mechanically laterally shifting said micro-hole collimator so that a central ray of said x-ray beam is not directly aligned with said aperture and wherein said circuitry samples said electrical signals to obtain an image produced by said x-ray beam on said detector array, and wherein said actuator laterally re-shifts said micro-hole collimator so that said central ray of said x-ray beam is directly aligned with said aperture and wherein said circuitry samples said electrical signals to obtain said magnified projection of said focal spot on said detector array, and wherein said computer subtracts said image from said magnified projection to compensate for radiation quanta proceeding through material of said micro-hole collimator.

* * * * *